(12) United States Patent  (10) Patent No.: US 7,867,212 B2
Waksmundzki et al.  (45) Date of Patent: Jan. 11, 2011

(54) ABSORBENT ARTICLES, FASTENER EARS FOR ABSORBENT ARTICLES, AND PROCESSES FOR MAKING SAME

(75) Inventors: Andrew Waksmundzki, Jackson, NJ (US); Mike Bond, Macon, GA (US)

(73) Assignee: First Quality Retail Services, LLC, Great Neck, NY (US)

( * ) Notice: Subject to any disclaimer, the term of this patent is extended or adjusted under 35 U.S.C. 154(b) by 876 days.

(21) Appl. No.: 11/524,840

(22) Filed: Sep. 21, 2006

(65) Prior Publication Data

US 2008/0077101 A1    Mar. 27, 2008

(51) Int. Cl.
A61F 13/15 (2006.01)
B65C 9/25 (2006.01)
B29C 65/00 (2006.01)
A44B 17/00 (2006.01)

(52) U.S. Cl. .................. 604/389; 604/387; 604/391; 604/390; 156/324; 156/543; 156/265; 24/586.1; 24/584.1

(58) Field of Classification Search ............... 24/586.1; 24/584.1; 156/324, 543, 265; 604/389, 387, 604/391, 390
See application file for complete search history.

(56) References Cited

U.S. PATENT DOCUMENTS

| | | | |
|---|---|---|---|
| 5,399,219 A | | 3/1995 | Roessler et al. |
| 5,900,101 A | * | 5/1999 | Justmann .................... 156/324 |
| 6,230,374 B1 | * | 5/2001 | Widlund .................... 24/586.1 |
| 6,788,803 B2 | | 9/2004 | Calvert |
| 6,820,671 B2 | | 11/2004 | Calvert |
| 2004/0016499 A1 | | 1/2004 | Miyamoto et al. |
| 2006/0246248 A1 | | 11/2006 | Van Dyke |
| 2006/0247596 A1 | | 11/2006 | Van Dyke |

FOREIGN PATENT DOCUMENTS

| | | |
|---|---|---|
| EP | 0 539 032 | 4/1993 |
| GB | 2 303 048 | 2/1997 |

OTHER PUBLICATIONS

European Search Report for EP 07 25 3506; Completed Feb. 7, 2008.

* cited by examiner

*Primary Examiner*—Jacqueline F. Stephens
(74) *Attorney, Agent, or Firm*—Amster, Rothstein & Ebenstein

(57) ABSTRACT

A method for manufacturing fastener ears for absorbent articles and other garments includes the step of cutting a wave-shaped pattern along the longitudinal axis of an elongated strip of material. The wave-shaped cutting pattern is substantially centered along the strip and divides the strip into a first web and a second web. Each web has a series of ear shapes, with each ear shape having a wave crest portion. Each wave crest portion has a first edge with a convex curvature. The method also includes the step of cutting each of the ear shapes out of its respective web to form a plurality of fastener ears. A fastener ear formed by such method is also contemplated.

13 Claims, 10 Drawing Sheets

ABSORBENT ARTICLES, FASTENER EARS FOR ABSORBENT ARTICLES, AND PROCESSES FOR MAKING SAME

FIELD OF THE INVENTION

The present invention relates generally to absorbent articles and fastener components for absorbent articles, and particularly to fastener ears and processes for manufacturing fastener ears that provide greater design flexibility while reducing or eliminating material waste.

BACKGROUND OF THE INVENTION

Absorbent articles, such as diapers and adult undergarments, are commonly secured around the wearer by hook and loop material or other types of fasteners that extend from the sides of the garment. The fasteners typically extend from the rear portion of the article and connect with a front portion of the article to secure the article around the waist of the wearer. In many articles, the fasteners are mounted on a stretch portion or "ear" which extends from the rear portion of the article. The ear functions as a pull tab to move the fastener into the desired position when the article is being secured.

Although fastener ears have been used in the art, there remains a need to improve the aesthetic and functional properties of the ears, while keeping the manufacturing process efficient.

SUMMARY OF THE INVENTION

The foregoing needs for an improved manufacturing process and for an improved fastener ear are resolved to a large degree by a manufacturing method in accordance with the present invention. In a first aspect of the invention, a method for manufacturing fastener ears includes the step of cutting a wave-shaped pattern generally along the longitudinal axis of an elongated strip of material. The wave-shaped pattern divides the strip into a first web and a second web. Each web has a series of ear shapes, with each ear shape having a wave crest portion comprising an edge with a convex curvature. The method also includes the step of separating each of the ear shapes from its respective web to form the fastener ears.

In a second aspect of the invention, a method of manufacturing fastener ears for an absorbent article includes the steps of cutting a strip of material in a composite cutting pattern along a generally longitudinal axis of the strip. The composite cutting pattern includes a first cut that follows a wave-shaped pattern, and a plurality of intermittent second cuts that are tangential to the wave-shaped pattern of the first cut. The first cut and plurality of second cuts form a nested pair of webs each comprising a series of ear shapes. The method also includes the step of separating the ear shapes from their respective webs to form the fastener ears.

In a third aspect of the invention, a fastener ear includes an ear formed by cutting a wave-shaped pattern generally along the longitudinal axis of an elongated strip of material. The wave-shaped pattern divides the strip into a first web and a second web. Each web has a series of ear shapes, with each ear shape having a wave crest portion comprising an edge with a convex curvature. The method also includes the step of separating each of the ear shapes from its respective web to form the fastener ears.

In a fourth aspect of the invention, an absorbent article includes a chassis and first and second fastener ears coupled to the chassis. Each fastener ear includes a wave crest portion comprising an upper edge and a lower edge. A portion of the upper edge of the first fastener ear corresponds to a portion of the lower edge of the second fastener ear. Another portion of the upper edge of the first fastener ear does not correspond to a portion of the lower edge of the second fastener ear.

BRIEF DESCRIPTION OF THE DRAWINGS

The foregoing summary and the following detailed description will be better understood in conjunction with the following drawing figures, in which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
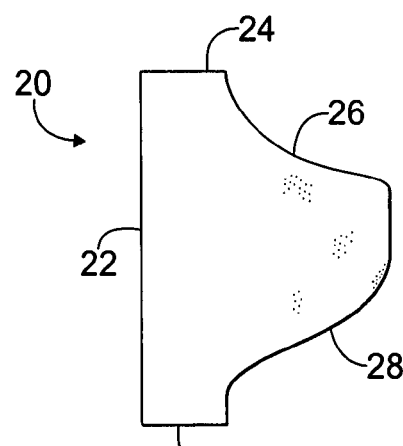
FIG. 1 is a plan view of a fastener ear in accordance with a first embodiment of the invention.

Referring to the drawing figures generally, and FIG. 1 in particular, an ear 20 in accordance with a first embodiment of the invention is shown. Ear 20 is designed for incorporation into an absorbent article to allow the article to be fastened or secured around the waist of the individual wearing the absorbent article. Ear 20 features a geometry that satisfies multiple competing interests, including but not limited to product appearance, product performance, manufacturing economies and waste minimization during the manufacturing process.

When absorbent articles are removed from packaging and unfolded, the rear and front portions must be distinguished from one another and oriented into the proper position relative to the wearer. Many times, the front portion of a diaper includes ears that make the front and rear portions appear very similar. This can make it difficult to correctly identify the front and rear portions of the diaper. Fastener ear 20 is configured with an asymmetrical configuration that visibly distinguishes the rear portion from the front portion. The asymmetrical configuration of the ear 20 assists the individual handling the article by helping the individual properly orient the article. In addition, the asymmetrical shape of the ear 20 provides a more aesthetically pleasing product appearance. Additionally, the shape of the ear 20 is selected to facilitate handling by the user of the absorbent article and to provide fit for user comfort and product performance.

Fastener ear 20 includes a first edge 22 that is generally linear. A second edge 24 extends from the first edge 22, extending transversely to the first edge. A third edge 26 extends from second edge 24. A substantial portion of third edge 26 has a concave curvature. A fourth edge 28 extends from third edge 26. A substantial portion of fourth edge 28 has a convex curvature. A fifth edge 30 extends from the fourth edge 28, extending transversely to the first edge. Fifth edge 30 connects first edge 22 with fourth edge 28. Collectively, first edge 22, second edge 24, third edge 26, fourth edge 28 and fifth edge 30 form a perimeter 32 of ear 20. The different contours, orientations, or curvatures of the third and fourth edges 26, 28 provide an asymmetrical configuration.

For purposes of this description, a "concave" edge refers to an edge having a majority of its length curving, bending or bowing inwardly toward the body of the tab. A "convex" edge refers to an edge having a majority of its length curving, bending or bowing outwardly and away from the body of the tab. Concave and convex edges may embody a variety of curvatures, including but not limited to circular, elliptical, parabolic, arcuate and other curvatures. The curvature of these edges may include a single curve or be made up of a combination of two or more different curves. Moreover, concave edges may contain a small section of convex curvature, so long as the majority of the edge has a concave curvature, and convex edges may contain a small section of concave curvature, so long as the majority of the edge has a convex curvature.

Ear 20 is attached to the rear portion (or optionally the front portion) of an absorbent article and is designed to be pulled around the sides of the wearer and attached to the front of the absorbent article. Ear 20 may be formed of either an elastomeric material or non-elastomeric material. In either case, ear 20 undergoes a certain amount of tensile stress when the ear is pulled around the waist of the wearer and connected with the front of the absorbent article. A wider portion of ear 20 is offset toward one side, allowing the wider portion to be positioned along or in proximity to the edge of the garment. In this arrangement, the ear fastens the garment securely around the wearer's waist by distributing tensile forces up near the waist line.

Figure 2:
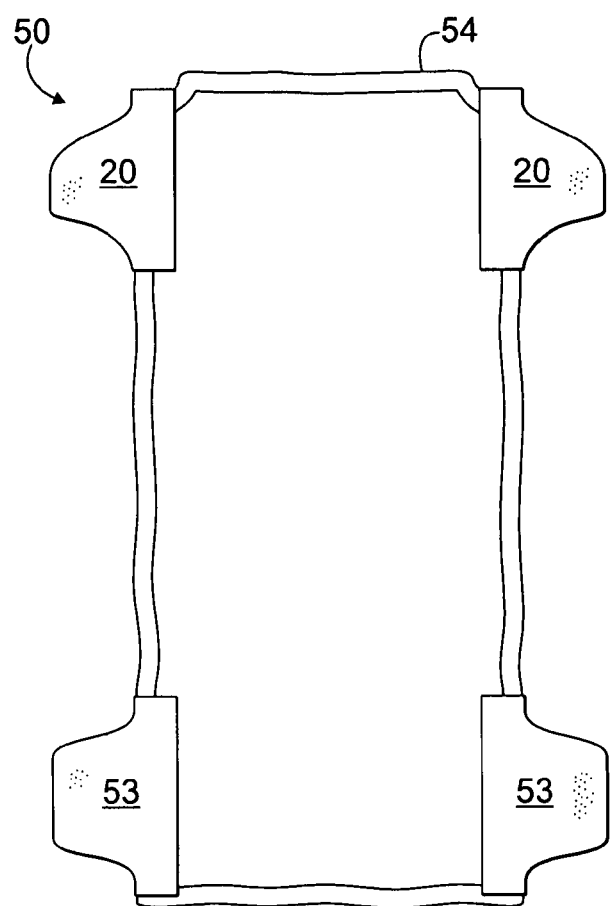
FIG. 2 is a plan view of an absorbent article incorporating the fastener ear configuration shown in FIG. 1.

Referring to FIG. 2, a garment 50 is shown with a front waist edge 52 and a rear waist edge 54 opposite the front waist edge. Front waste edge 52 has a pair of front ears 53 each having a substantially symmetrical configuration, and rear waist edge 54 has a pair of rear ears 20 each having an asymmetrical configuration. Rear ears 20 are noticeably larger than front ears 53, but may be any size. In addition, the asymmetrical shape of rear ears 20 provides a visibly apparent contrast to the symmetrical shape of front ears 53. In this arrangement, rear ears 20 provide a readily identifiable means of distinguishing the rear portion of the article from the front portion.

Rear ears 20 are attached to the article 50 in a mirrored arrangement. In view of this, it is desirable to manufacture a set or "web" of ears having one configuration, and a mirrored set or "web" of ears having the reverse configuration. In this way, ears from one web can be processed and attached to one side of the absorbent product, and ears from the other mirrored web can be processed and attached to the opposite side of the absorbent product.

Figure 3:
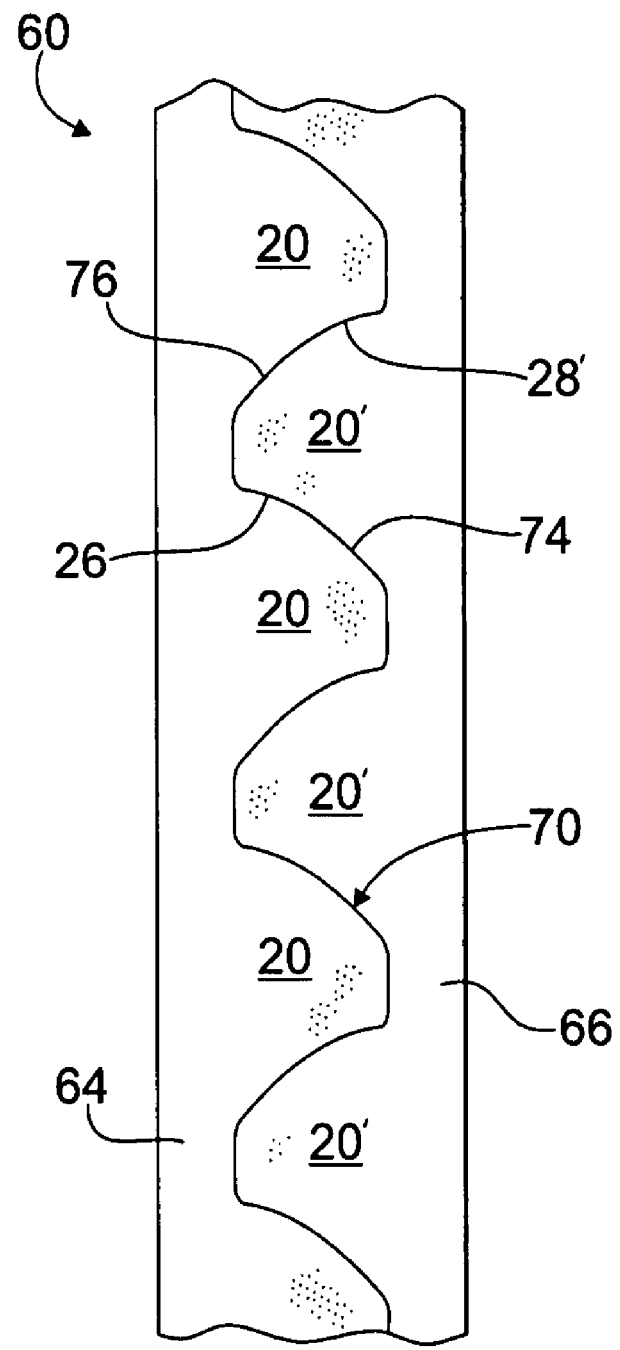
FIG. 3 is a truncated plan view of a strip of material being processed in a first step of an exemplary process in accordance with the invention.

Referring now to FIG. 3, fastener ears are shown as they would be manufactured in accordance with one process of the invention. As will be explained, the geometry of the ears of the present invention allow mass production of mirrored webs from a single strip or length of stock material. In addition, the geometry of the ears allows the mirrored webs to be produced with little or no material going to waste. A strip of stock material 60 is shown as it would appear after two mirrored webs are cut but not separated from one another.

Strip 60 includes a central wave-shaped cut 70 that produces two webs of ears in a nested arrangement. The nested arrangement allows all of the strip to be incorporated into the ears, with no material left over as waste or scrap. A first web 64 of ears is produced on a first side of the wave-shaped cut 70, and a second web 66 of ears is produced on a second side of the wave-shaped cut opposite the first side. For purposes of description, elements in first web 64 are identified with a specific reference number, and corresponding elements in second web 66 are identified with the same reference number accompanied by a prime symbol ('). Thus, first web 64 includes a series of lobes or ear shapes 20 and second web 66 includes a series of lobes or ear shapes 20'.

Wave-shaped cut 70 is configured so that ears 20 and 20' are mirror images of one another, albeit in an offset or shifted relationship. For purposes of this description, wave-shaped cut 70 is described as approximating a sinusoidal wave pattern, with ears 20 and 20' arranged ninety degrees out of phase. This is accomplished by a cutting pattern that includes a first wave section 74 and a second wave section 76 having an equal length and curvature as the first wave section. The second section 76 of wave-shaped cut 70 follows a pattern that is the reverse of the first section 74 of the cut with respect to the axis of strip 60. In this pattern, the first and second wave sections 74 and 76 have opposing curvatures that constitute reverse images of one another. For purposes of this description, this type of wave will be referred to as a "reversing" wave. In a reversing wave, the cut made to form one edge on a first web simultaneously forms a contiguous edge on the second web. Referring to FIG. 3, for example, the reversing wave-shaped cut 70 forms third edge 26 on first web 64 and simultaneously forms fourth edge 28' on second web 66.

Figure 4:
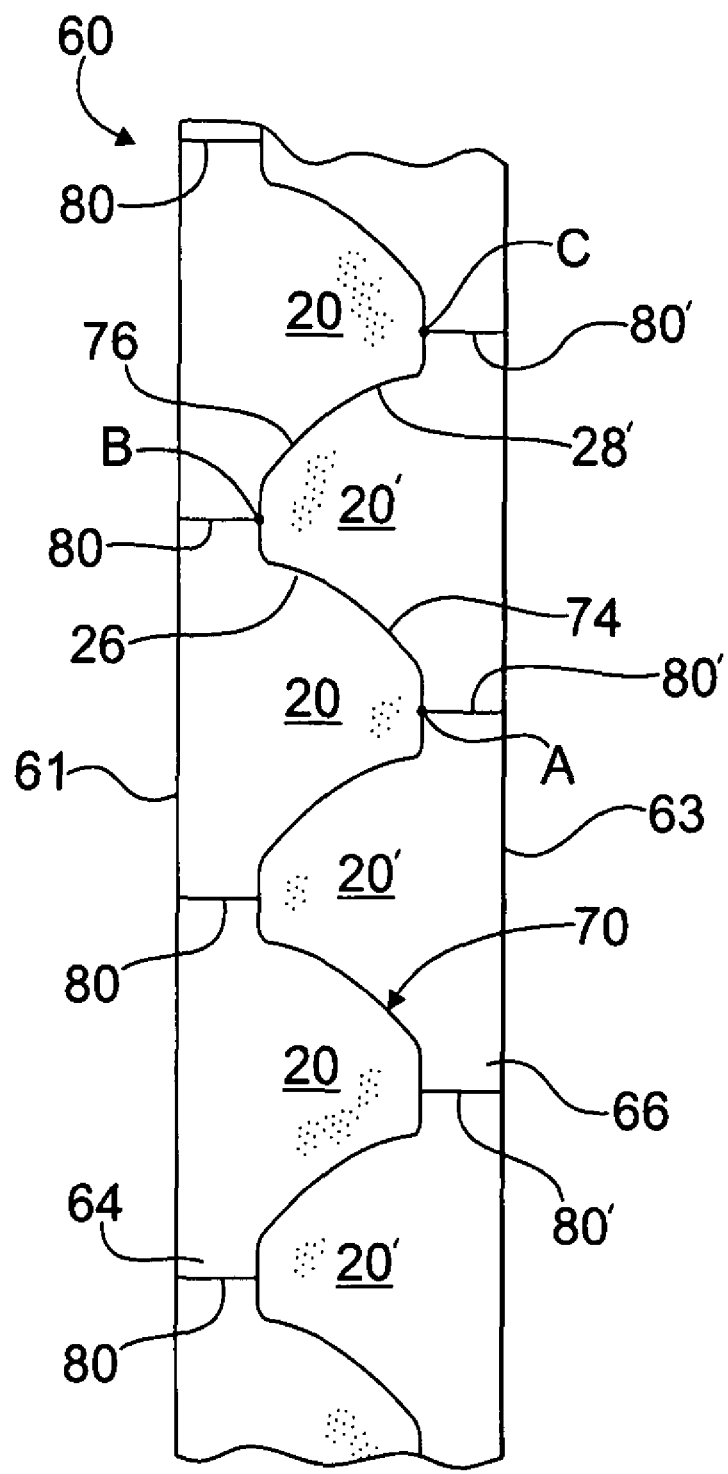
FIG. 4 is a truncated plan view of a strip of material being processed in a second step of an exemplary process in accordance with the invention.

Once the two webs 64 and 66 are formed on strip 60, a series of cross-cuts or transverse cuts can be made to divide the webs into individual ears. Referring now to FIG. 4, first web 64 includes a series of incrementally spaced transverse cuts 80, and second web 66 includes a series of incrementally spaced transverse cuts 80'. Transverse cuts 80, 80' intersect the wave-shaped cut 70 to divide the strip into multiple fastener ears. Ear shapes 20 are nested in ear shapes 20' and vice versa, so that the ear shapes are contiguous with one another. The transverse cuts 80, 80' are shown on strip 60 prior to separation of first and second webs 64, 66. It is noted, however, that the transverse cuts 80, 80' can be made after the webs 64, 66 are separated. Moreover, it may be desirable to separate the webs, bring the ears into phase with one another, and make a single transverse cut across both webs. A process for manufacturing the fastener ears will be described in more detail below.

Strip 60 has a first side edge 61 and a second side 63, each side edge extending the length of the strip. First side edge 61 extends adjacent the first web 64 of ears 20, and second side edge 63 extends adjacent the second web 66 of ears 20'.

First and second wave sections 74, 76 begin and end where reversing wave cut 70 intersects the transverse cuts, as exemplified by points "A", "B" and "C" in FIG. 4. For example, each first wave section 74 begins at a point where a transverse cut 80' in the second web 66 intersects the wave-shaped cut 70 (point "A"), and ends where another transverse cut 80 in the first web 64 intersects the wave-shaped cut (point "B"). A second wave section 76 then begins at the transverse cut 80 where the first wave section 74 ends (point "B"), and ends at another transverse cut 80' in the second web 66 (point "C"). In this arrangement, the perimeter of each ear 20 is defined by a portion of first side edge 61, a first wave section 74 of the cut 70, a second wave section 76 of the cut, and a pair of transverse cuts 80 made in the first web 64. Similarly, the perimeter of each ear 20' is defined by a portion of second side edge 63, a first wave section 74 of the cut 70, a second wave section 76 of the cut, and a pair of transverse cuts 80' made in the second web 66. The wave-shaped cut 70 and transverse cuts 80 and 80' define the respective perimeters of ear shapes 20 and 20'. As a result, ear shapes 20 and 20' can be split apart along the wave-shaped cut 70 and transverse cuts 80 and 80'.

Figure 5:
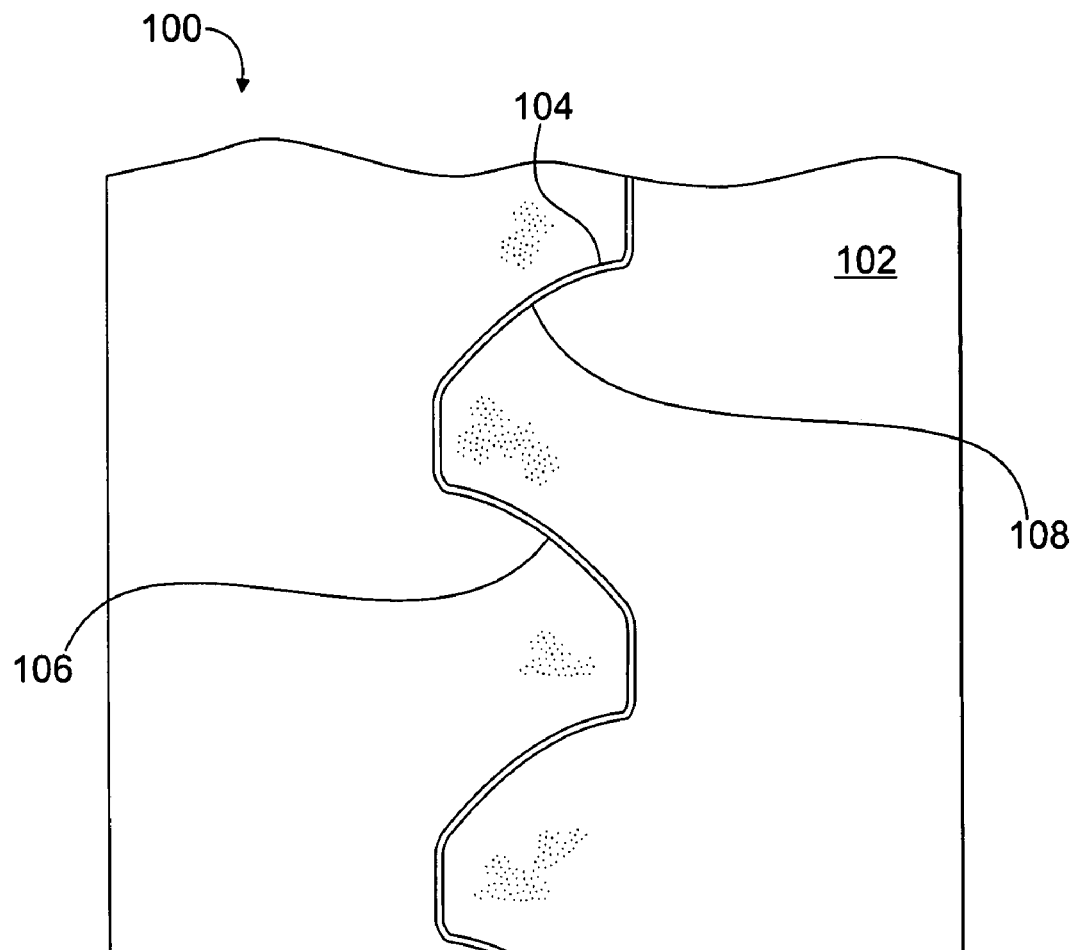
FIG. 5 is an elevation view of an exemplary cutting die used in a process for manufacturing fastener ears in accordance with the invention.

The ears 20 may be cut using a number of techniques. For purposes of this description, the ears 20 will be described assuming they are manufactured using a rotary die cutting process. One of ordinary skill in this area of technology will understand that there are other cutting methods and techniques for manufacturing the ears 20, and die cutting is referred to only for purposes of illustration. Referring to FIG. 5, a rotary die 100 is shown. Rotary die 100 has a cylindrical body 102 and a cutting blade 104 that projects from the circumference of the die. Cutting blade 104 follows a wave-shaped pattern, which, for purposes of description, can be divided into a number of first blade sections 106 and a number of second blade sections 108. The first blade sections 106 are of the same length as the second blade sections 108, but are oriented in the opposite direction. Cutting blade 104 is configured to make a cut into a strip of material which is passed between the rotary die 100 and an anvil.

Figure 6:
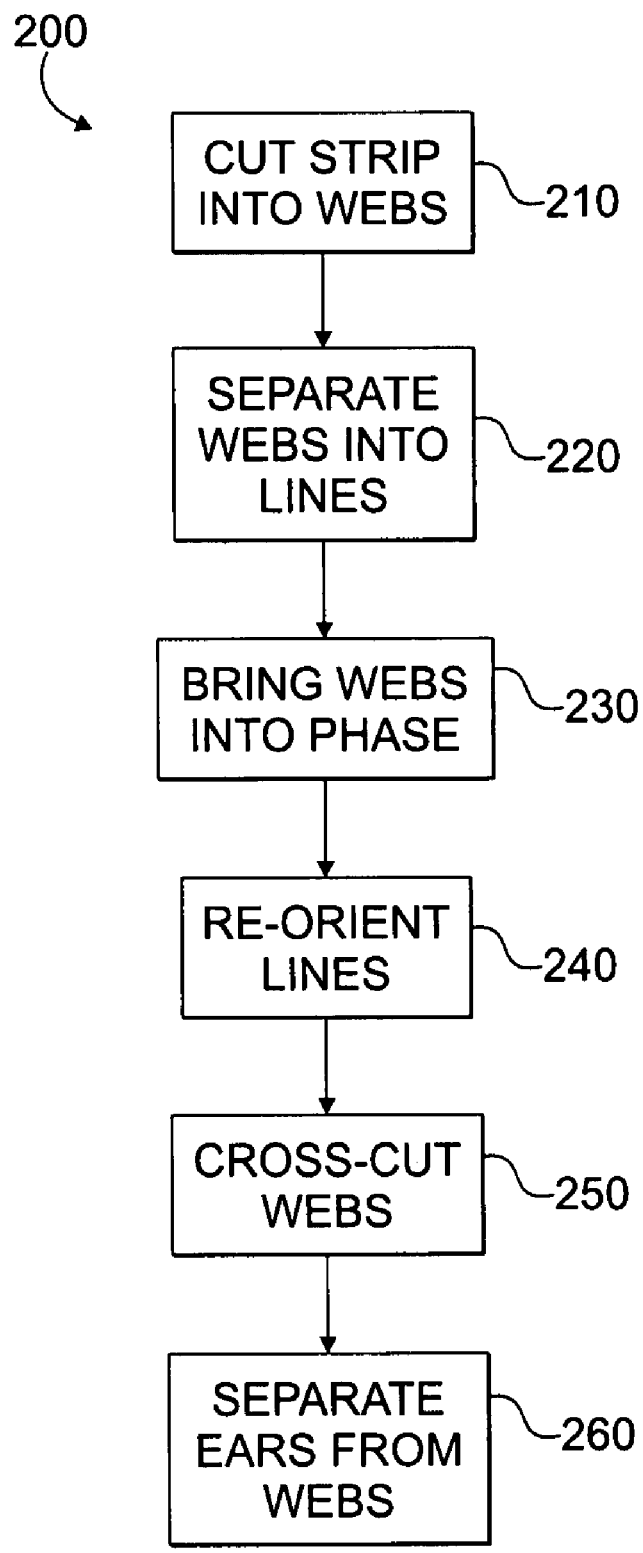
FIG. 6 is a block diagram illustrating steps of an exemplary process for manufacturing fastener ears in accordance with the invention.

Referring now to FIG. 6, a method for manufacturing fastener ears in accordance with a first exemplary process 200 of the invention is shown. Referring to step 210, a strip of material is initially passed through a cutting machine, such as the rotary die shown in FIG. 5. The material is delivered to the cutting machine in any conventional manner. For example, roll stock material may be unwound off of a large roll and run through the machine. If a rotary die is used, material is passed between the die blade and an anvil. A wave-shaped cut is made through the center portion of the material to divide the strip into two nested or meshed webs. Because two symmetrical webs are to be formed in the material, the material should be axially aligned in the machine direction with the axis of the wave-shaped blade of the die, ensuring that the cut is centered or substantially centered along the strip of material.

Once the wave-shaped cut is made, the meshed webs are separated in step 220 into two separate lines. As noted above, the webs are initially cut with the two webs ninety degrees out of phase. The webs are therefore brought into phase with one another in step 230. This may be accomplished by running one web over a longer distance than the other web, the extra distance corresponding to the initial phase difference between the webs. For the cut shown in FIG. 3, this will correspond to half the length of an ear 20.

The two webs are initially formed with the ear sections facing one another. In the finished product, however, the fastener ears preferably face the opposite direction, or away from one another, as shown for example in FIG. 2. Therefore, the webs are reoriented in step 240 so that the crests or narrow edges of the ears are oriented away from one another. This may be accomplished by inverting one or both webs and crossing their paths as necessary so that the flat uncut edges of the webs face one another. The two webs are oriented in a substantially coplanar arrangement with the ear sections registered in symmetry (i.e. the crest sections are in phase with one another as illustrated in FIG. 2). A single transverse cut is then made through the narrow portions of the webs in step 250 to divide each web into individual fastener ears. The individual fastener ears are physically separated from the webs in step 260.

Although the steps are shown and described in an exemplary order in FIG. 6, the steps can be performed in a variety of orders. Also, steps are optionally removed or added as needed.

In some applications, it may be desirable to use a wave shape that is more complex than a reversing wave. That is, it may be desirable to form a wave-shaped cut in which adjacent sections of the wave vary from one another in terms of length, curvature or both (i.e. a "non-reversing" wave). Non-reversing waves provide greater flexibility in design, since the edges of the ears need not have sections with the same length and/or curvature. More complex geometries may be selected, which enhances the appearance of the product. Notwithstanding the benefits of non-reversing wave shapes, it is equally desirable to retain the advantages of a contiguous or nested arrangement.

Figure 7:
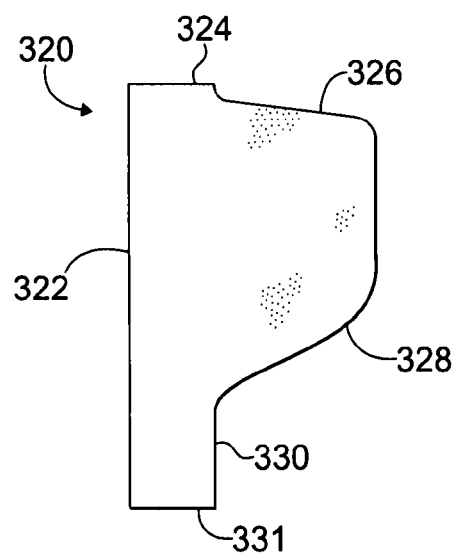
FIG. 7 is a plan view of a fastener ear in accordance with another embodiment of the invention.

Referring now to FIG. 7, a fastener ear 320 manufactured from a non-reversing wave-shaped cut is shown in accordance with a second embodiment of the invention. The perimeter of ear 320 includes wave sections that vary in terms of length and curvature. Ear 320 includes a first edge 322 that is generally linear. This first edge 322 is optionally coupled to a chassis of an absorbent article. A second edge 324 extends from the first edge 322, extending transversely to the first edge. A third edge 326 which is substantially linear (but optionally curved) extends from second edge 324. A fourth edge 328 having a convex curvature extends from third edge 326. A fifth edge 330 extends from the fourth edge 328, extending generally parallel to first edge 322. Finally, a sixth edge 331 connects first edge 322 with fifth edge 330. Collectively, first edge 322, second edge 324, third edge 326, fourth edge 328, fifth edge 330 and sixth edge 331 form a perimeter 332 of ear 320. The different lengths and curvatures of third and fourth edges 326 and 328 provide an asymmetrical configuration which visibly contrasts with the front portion of an absorbent article.

Figure 8:
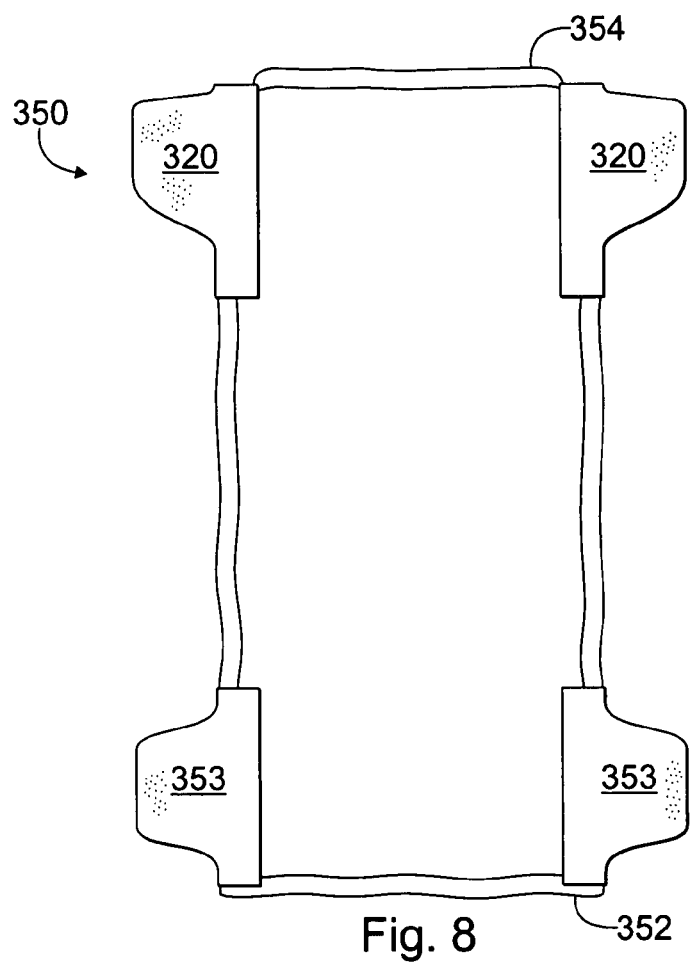
FIG. 8 is a plan view of an absorbent article incorporating the fastener ear configuration shown in FIG. 7.

Referring to FIG. 8, a garment 350 is shown with a front waist edge 352 and a rear waist edge 354 opposite the front waist edge. Front waste edge 352 has a pair of front ears 353 having a substantially symmetrical configuration, and rear waist edge 354 has a pair of rear ears 320 having an asymmetrical configuration. Rear ears 320 are noticeably larger than front ears 353, but may be any size. In addition, the asymmetrical shape of rear ears 320 contrasts visually with the symmetrical shape of front ears 353. In this arrangement, rear ears 320 provide a readily identifiable means of distinguishing the rear portion of the article from the front portion.

As noted above, there are advantages in manufacturing a web of ears having one configuration, and a mirrored set or "web" of ears having the reverse configuration. Moreover, it is preferable to manufacture ears in a nested arrangement from a single strip of material, as exemplified by tabs 20, 20' in FIG. 4. The non-reversing wave shape used to form ears 320 can not be made from a single cut through the center of a strip, however, as in the case of tabs 20, 20'. This is due to the fact that the third and fourth edges 326 and 328 (which can alternatively be considered to be upper and lower edges of the tabs 20, 20') are different with respect to length and curvature.

A cut that defines a third edge 326 on one web will not define a fourth edge 328 on a nested web, because the two edges are of different length and/or shape or curvature, and cannot be completely contiguous. Of course, one could optionally manufacture two opposing webs from two separate strips of material, but this would create additional trim waste, since only one side of each strip would be incorporated into the ears. In addition, the resulting manufacturing process would be inefficient, because two separate lines of ears would have to be cut and brought together in phase before being combined with an absorbent body. Operating an assembly line with two separately-cut webs would therefore be more difficult and less efficient than cutting nested webs from a single strip of material.

Applicant has developed ears having a complex non-reversing wave shape and a corresponding process for manufacturing a nested arrangement of ears having the complex non-reversing wave shape, where the nested webs are cut simultaneously in a single step. The process can be applied to a variety of non-reversing wave shapes, such as the ear configurations shown in FIGS. 4 and 5. According to one exemplary embodiment of a process according to the invention, the nested webs are cut by means of a composite cutting pattern in which a single cutting line splits into two lines and merges back into a single cutting line. This process allows for the formation of ears having a variety of configurations and permits a manufacturer to produce a more aesthetic or functional product design from a single strip of material. The mirrored webs are simultaneously cut in a nested arrangement to produce two webs while minimizing trim waste.

Figure 9:
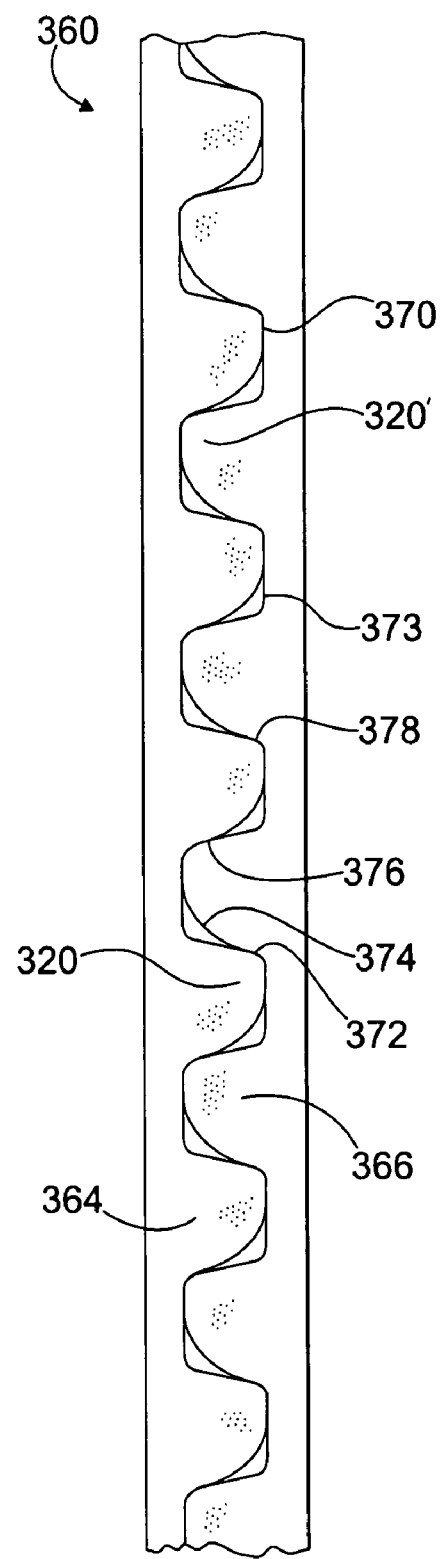
FIG. 9 is a truncated plan view of a strip of material being processed in a first step of another exemplary process in accordance with the invention.

Referring now to FIG. 9, a strip of material 360 is shown in which a non-reversing wave-shaped cut is made to produce webs in a mirrored web arrangement. Strip 360 includes a central wave-shaped cut 370 that produces two webs of ears in a nested arrangement. The nested arrangement allows almost all material of the strip 360 to be incorporated into the ears, with minimal material left over as waste or scrap. A first web 364 of ears is produced on a first side of the wave-shaped cut 370, and a second web 366 of ears is produced on a second side of the wave-shaped cut opposite the first side. As before, elements in first web 364 are identified with a specific reference number, and corresponding elements in second web 366 are identified with the same reference number accompanied by a prime symbol ('). Thus, first web 364 includes a series of ear shaped sections or ear shapes 320 and second web 366 includes a series of ear shapes 320'.

Wave-shaped cut 370 is configured so that ear shapes 320 and 320' are mirror images of one another, albeit in an offset or shifted relationship. For purposes of this description, wave-shaped cut 370 is described as approximating a sinusoidal wave pattern, with ears 320 and 320' having wave crest portions formed by the cut that are ninety degrees out of phase. This is accomplished by using a composite cutting pattern that includes a primary cut line 372 and a secondary cut line 374. Primary cut line 372 follows a substantially trapezoidal pattern. As such, primary cut line 372 includes a first segment 376 and a second segment 378 that are of equal length and opposite angular orientation. In this arrangement, primary cut line 372 forms a reversing wave pattern of lobes, similar to the reversing pattern in FIG. 3.

Secondary cut line 374 removes a small portion or wedge of each lobe that is left by primary cut line 372, so that the final cut edge on each of the nested webs is non-reversing. This leaves a small aperture 373 in the strip 360, which corresponds to a small portion of wasted material (or design waste). Ears 320 are nested in ears 320', and vice versa, so that the ear shapes are partially contiguous with one another.

As can be observed, a portion of the upper edge 326 of each ear 320 is contiguous with and corresponds to a portion of the lower edge 328' of each ear 320'. There is also a portion of upper edge 326 of each ear 320 that is not contiguous with, and therefore does not correspond to, the lower edge 328' of each ear 320'. The partially contiguous relationship between ears 320 and 320' provides the ability to nest the first and second webs 364 and 366 along the contiguous portions, while providing more flexibility of design along the non-contiguous portions. The non-contiguous portions of ears 320 and 320' can be designed with a variety of configurations because their respective shapes are independent of one another.

Figure 10:
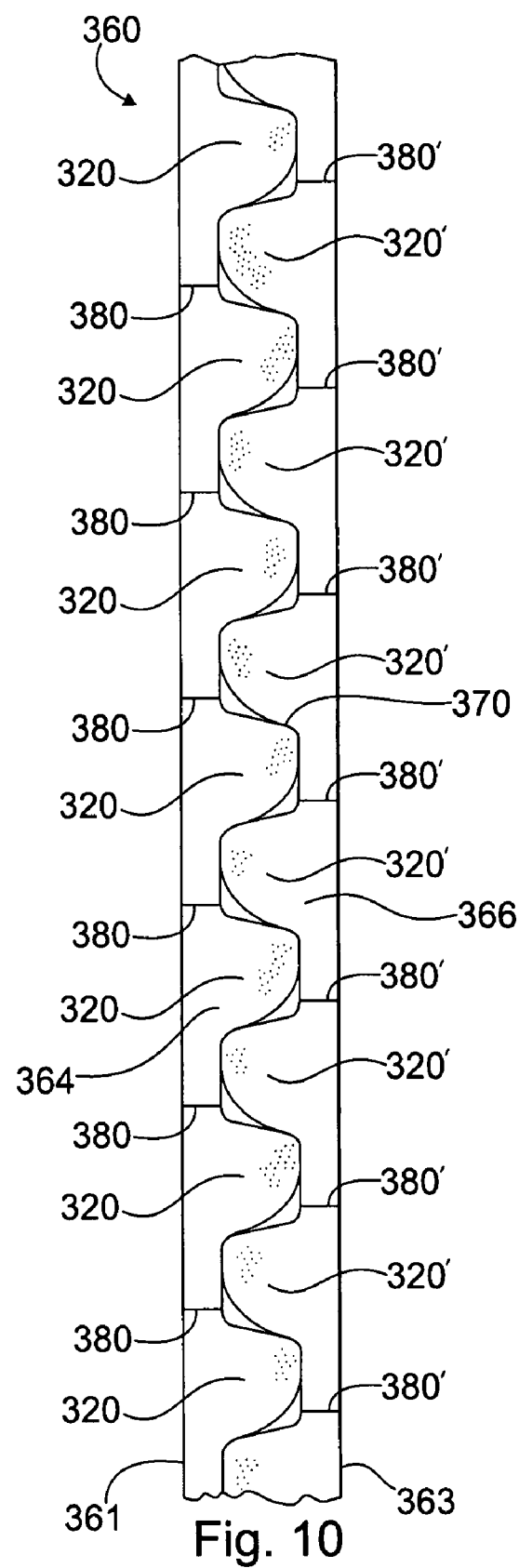
FIG. 10 is a truncated plan view of a strip of material being processed in a second step of another exemplary process in accordance with the invention.

Once the two webs 364 and 366 are formed on strip 360, a series of cross-cuts or transverse cuts can be made to divide the webs into individual ears. Referring now to FIG. 10, first web 364 includes a series of incrementally spaced transverse cuts 380, and second web 366 includes a series of incrementally spaced transverse cuts 380'. Transverse cuts 380, 380' intersect the wave-shaped cut 370 to divide the strip into multiple fastener ears 320, 320'. For purposes of illustration, transverse cuts 380, 380' are shown on strip 360 prior to separation of first and second webs 364, 366. It is noted, however, that the transverse cuts 380, 380' can be made after the webs 364, 366 are separated. For example, it may be desirable to separate the webs, bring the ears into phase with one another, and make a single transverse cut across both webs. A process for manufacturing the fastener ears 320, 320' will be described in more detail below.

Strip 360 has a first side edge 361 and a second side 363, each side edge extending the length of the strip. First side edge 361 extends adjacent the first web 364 of ears 320, and second side edge 363 extends adjacent the second web 366 of ears 320'.

The fastener ears 320, 320' begin and end where primary cut line 372 intersects the transverse cuts 380, 380'. Transverse cuts 380, 380' do not intersect the secondary cut line 374. The composite wave-shaped cut 370 and transverse cuts 380 and 380' define the respective perimeters of ear shapes 320 and 320'. As a result, ear shapes 320 and 320' can be split apart along the composite wave-shaped cut 370 and transverse cuts 380 and 380'.

Figure 11:
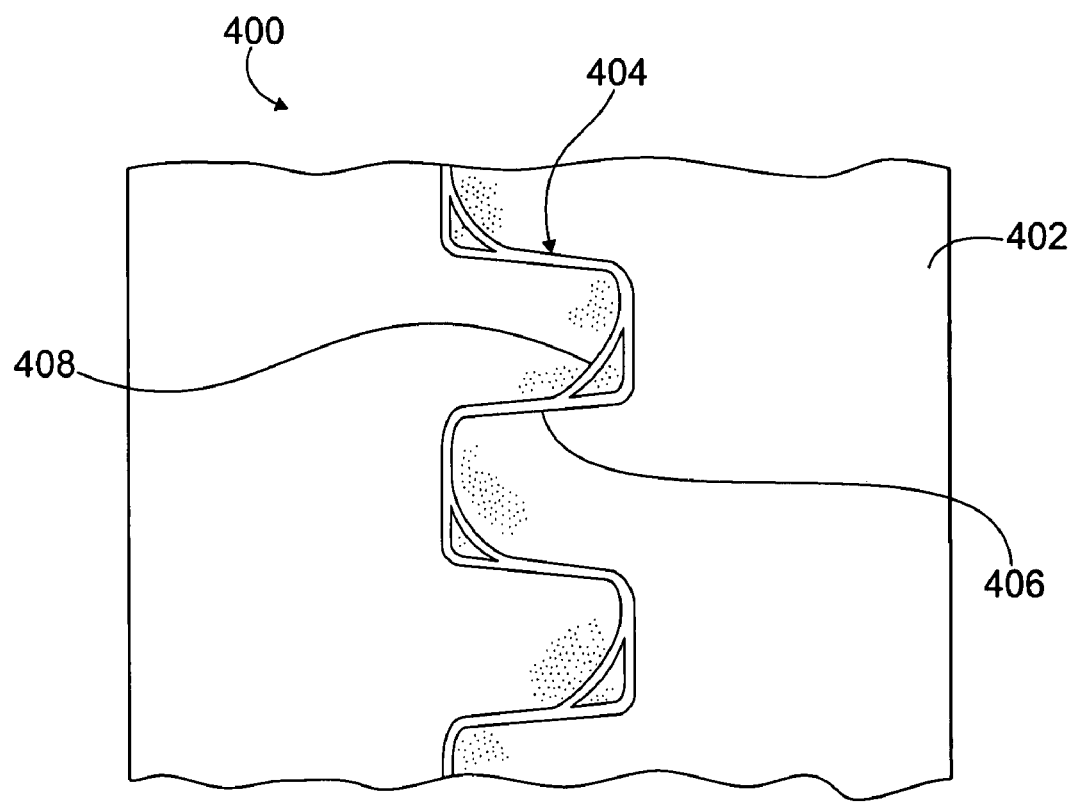
FIG. 11 is an elevation view of another exemplary cutting die used in a process for manufacturing fastener ears in accordance with the invention.

As noted above, the ears of the present invention may be cut using a number of techniques. Ears 320 will be described assuming they are manufactured using a rotary die cutting process. One of ordinary skill in this area of technology will understand that there are other cutting methods and techniques for manufacturing the ears 320, and die cutting is referred to only for purposes of illustration. Referring to FIG. 11, a rotary die 400 is shown. Rotary die 400 has a cylindrical body 402 and a cutting blade 404 that projects from the circumference of the die.

Cutting blade 404 follows a wave-shaped pattern, which, for purposes of description, can be divided into a primary blade section 406 and a number of secondary blade sections 408. Primary blade section 406 follows a generally trapezoidal pattern. Secondary blade section 408 periodically diverges from primary blade 206 and follows a generally arc-shaped path (or any selected path) before merging back with the primary blade section. Each of blade sections 406 and 408 is configured to make a cut into a strip of material which is passed between rotary die 400 and an anvil. The blade sections 406 and 408 simultaneously cut into the strip of material, producing a composite cut in a single step. Secondary blade section 408 removes a portion of each lobe which lies inside the primary cut line 372, producing a small wedge or piece of scrap material.

The wedge of material corresponding to the portion between blade sections 406 and 408 represents a small percentage of the total area of each fastener ear. The size of the wedge is preferably less than about 20 percent of the total area of the ear, more preferably less than about 15 percent, still more preferably less than about 10 percent, and most preferably less than about 5 percent. The area of the wedge may be larger than about 20 percent of the total area of the ear and still produce satisfactory results in accordance with the invention, however. The small amount of waste produced by these wedges is insignificant when compared to the amount of material and production time that can be saved using the nested web arrangement. Also, the flexibility in ear shape and design choice made possible by the wedges are significant benefits.

Figure 12:
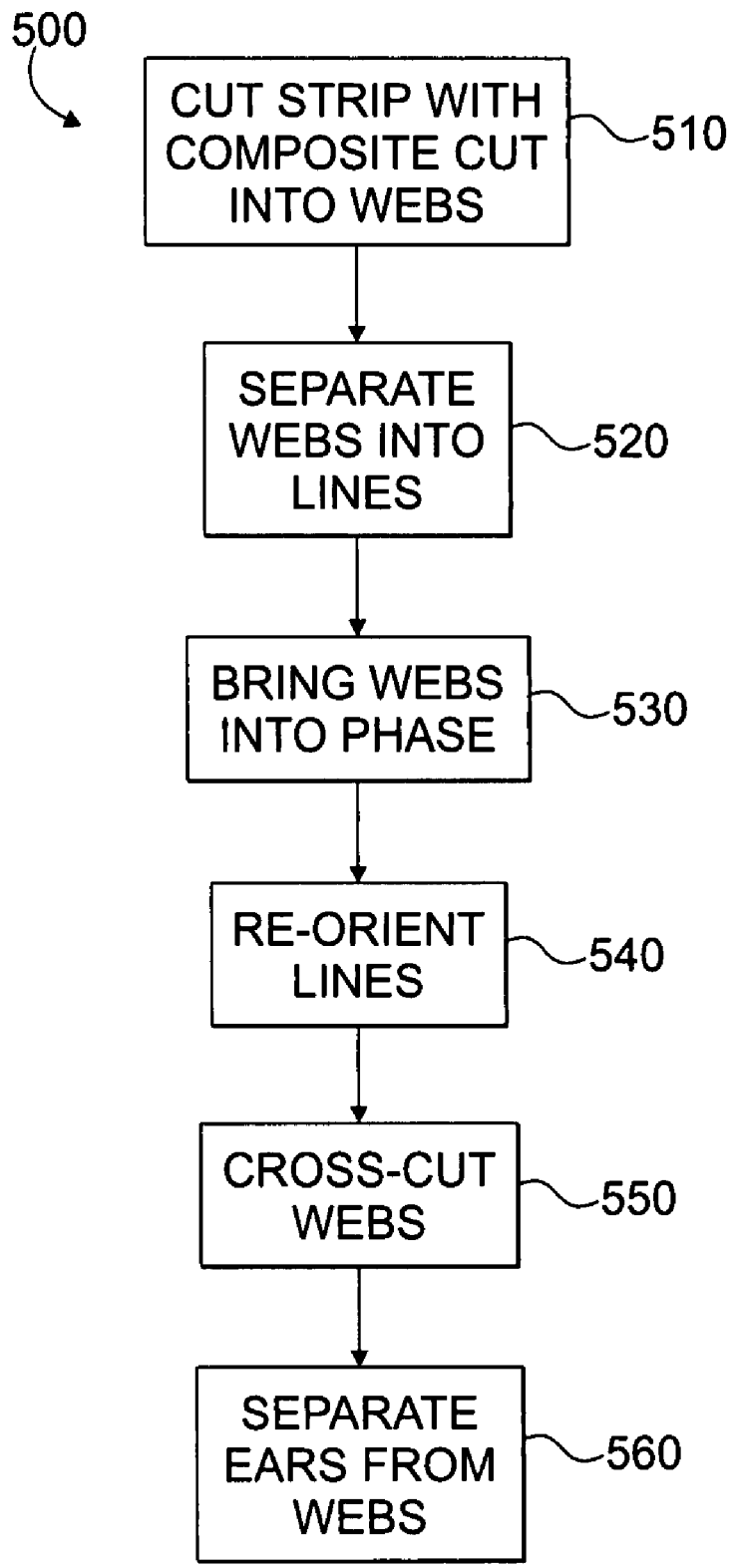
FIG. 12 is a block diagram illustrating steps of another exemplary process for manufacturing fastener ears in accordance with the invention.

Referring now to FIG. 12, a method for manufacturing fastener ears in accordance with a second process 500 of the invention is shown. Referring to step 510, a strip of material is initially run through a cutting machine, such as the rotary die shown in FIG. 11. Where a rotary die is used, the material is passed between the die blade and an anvil. A composite wave-shaped cut is made through the center portion of the material to divide the strip into two nested or meshed webs. Because two symmetrical webs are to be formed in the material, the material should be axially aligned in the machine direction with the axis of the wave-shaped blade of the die, ensuring that the composite cut is centered or substantially centered along the strip of material.

Once the composite wave-shaped cut is made, the wedge portion is removed from the line by vacuum suction or other means for clearing scrap. The webs are then separated into two separate lines in step 520. The webs are initially meshed with the wave crests ninety degrees out of phase. The webs are therefore brought into phase with one another in step 530. This may be accomplished by running one web over a longer distance than the other web, the extra distance corresponding to the initial phase difference between the webs. For the cut shown in FIG. 9, this will correspond to half the length of an ear shape 320.

The webs, which are initially positioned with the wave crests facing toward one another, are reoriented in step 540 so that the crests are oriented away from one another. This may be accomplished by inverting one or both webs and crossing their paths as necessary so that the wave crests face away from one another. The two webs are oriented in a substantially coplanar arrangement with the ear sections registered in symmetry (i.e. the crest sections are in phase with one another). A single transverse cut is then made through the narrow portions of the webs in step 550 to divide each web into individual fastener ears. The individual fastener ears are physically separated from the webs in step 560.

Although the steps are shown and described in an exemplary order, the steps can be performed in a variety of orders. Also, steps are optionally removed or added as needed.

While preferred embodiments of the invention have been shown and described herein, it will be understood that such embodiments are provided by way of example only. Numerous variations, changes and substitutions will occur to those skilled in the art without departing from the spirit of the invention. For example, although manufacturing processes have been described with transverse cuts being made after the webs are separated and brought into phase with one another, transverse cuts may be made prior to separation of the webs. In addition, the primary cut line may follow a rectangular wave pattern, as an alternative to a trapezoidal wave. Accordingly, it is intended that the appended claims cover all such variations as fall within the spirit and scope of the invention.

What is claimed:

1. A method of manufacturing fastener ears for an absorbent article comprising the steps of:
    cutting a wave-shaped pattern generally along the longitudinal axis of an elongated strip of material, said wave-shaped pattern dividing the strip into a first web and a second web, each web having a series of asymmetrical ear shapes, each asymmetrical ear shape having a wave crest portion comprising first edge with a convex curvature and a second edge opposite from the first edge that varies from the first edge in terms of at least one of length and curvature; and
    separating each of the asymmetrical ear shapes from its respective web to form the fastener ears.

2. The method of claim 1, wherein said second edge is linear.

3. The method of claim 2, wherein said cutting step comprises forming the convex edge on each ear shape adjacent to the linear edge on the ear shape.

4. The method of claim 2, wherein said cutting step comprises forming the convex edges in the first web contiguous with the linear edges in the second web.

5. The method of claim 4, wherein said cutting step comprises forming the convex edges in the second web contiguous with the linear edges in the first web.

6. The method of claim 2, wherein said separating step comprises cutting each web at a point located between a convex edge and a linear edge.

7. The method of claim 2, wherein said separating step comprises cutting each web at a point located between a convex edge and a linear edge in a direction substantially perpendicular to the longitudinal axis of the strip.

8. The method of claim 1 wherein said cutting step comprises incorporating at least about 95 percent of the strip of material into the plurality of fastener ears.

9. The method of claim 1 wherein said cutting step comprises incorporating about 100 percent of the strip of material into the plurality of fastener ears.

10. The method of claim 1, wherein the step of cutting a wave-shaped pattern comprises making a composite cut with only one rotary die.

11. The method of claim 10, wherein the rotary die used in said cutting step comprises a cutting edge having a primary cutting blade portion extending around the circumference of the die in a wave-shaped pattern, and a plurality of secondary cutting blade portions each lying tangentially to portions of the primary cutting blade portion.

12. The method of claim 11, wherein the primary cutting blade portion of the rotary die used in said cutting step follows a generally trapezoidal pattern, and the secondary cutting blade portions are arcuate.

13. A fastener ear produced from the process of claim 1.

* * * * *